US00PP14011P29

(12) United States Plant Patent
Utecht

(10) Patent No.: US PP14,011 P2
(45) Date of Patent: Jul. 22, 2003

(54) GERANIUM PLANT NAMED 'FIP 750'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/259,583

(22) Filed: Sep. 30, 2002

(51) Int. Cl.[7] ..... A01H 5/00
(52) U.S. Cl. ..... Plt./325

(58) Field of Search ..... Plt./325

*Primary Examiner*—Kent Bell
(74) *Attorney, Agent, or Firm*—Foley & Lardner

(57) ABSTRACT

A new and distinct cultivar of geranium plant named 'Fip 750' characterized by the combined features of brilliant, purple-violet flowers with white markings, semi-double flower type, dark-green foliage with weak zonation, relatively large umbels, compact, tight plant habit, and early to medium spring flowering response.

1 Drawing Sheet

Latin name of the genus and species of the plant claimed: *Pelarognium zonale* L'Héritier.

Variety denomination: 'Fip 750'.

BACKGROUND OF THE INVENTION

The present invention comprises a new and distinct cultivar of geranium, botanically known as *Pelargonium zonale,* and hereinafter referred to by the cultivar name 'Fip 750'.

'Fip 750' is a product of a planned breeding program which had the objective of creating new zonal geranium cultivars with violet to lavender flower color in combination with dark-green foliage.

'Fip 750' originated from a hybridization made by the inventor Angelika Utecht in a controlled breeding program in Galdar, Gran Canaria, Spain, in 1995.

The female parent was an unpatented hybrid seedling, No. 92-876-2, having purple, single-type flowers with orange markings, large umbels, dark-green, distinctly zoned foliage, and medium to vigorous growth habit. The male parent of 'Fip 750 ' was a self-seedling of the commercial, unpatented variety 'Novave'. This seedling was characterized by dark-rose to purple, semi-double flowers, large, medium-green leaves with distinct zonation, and medium sized plant habit, while variety 'Novave' has a lighter purple-pink tone of flower and somewhat less distinct zonation.

'Fip 750' was selected as one flowering plant within the progeny of the stated cross by Angelika Utecht in 1996 in a controlled environment in Galdar, Gran Canaria, Spain. The first act of asexual reproduction of 'Fip 750' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from cuttings of the plant initiated in May 1999 in Hillscheid, Federal Republic of Germany, and continuing thereafter, has demonstrated that the combination of characteristics as herein disclosed for 'Fip 750' are firmly fixed and are retained through successive generations of asexual reproduction.

'Fip 750' has not been observed under all possible environmental conditions. The phenotype may vary significantly with variations in environment such as temperature, light intensity and day length.

The following observations, measurements, and comparisons describe plants grown in Hillscheid, Germany, under greenhouse conditions which approximate those generally used in commercial practice.

BRIEF SUMMARY OF THE INVENTION

The following traits have been repeatedly observed and are determined to be basic characteristics of 'Fip 750' in combination distinguish this geranium as a new and distinct cultivar:

1. Brilliant purple-violet flowers with white markings;
2. relatively large inflorescences, well above the foliage;
3. dark green foliage with weak zonation;
4. compact and very well branched plant habit; and
5. early to medium spring flowering response.

Of the many commercial cultivars known to the present inventor, the most similar in comparison to 'Fip 750' is the related variety 'Novave' (unpatented). In comparison to 'Novave', 'Fip 750' has a deeper shade of flower color, and dark-green, instead of medium-green, leaves.

BRIEF DESCRIPTION OF THE DRAWING

The accompanying photographic drawing shows typical flower and foliage characteristics of 'Fip 750' with colors being as true as possible with an illustration of this type. The drawing depicts a side elevational view of a typcial flowering potted plant of 'Fip 750'.

DETAILED BOTANICAL DESCRIPTION

The measurements were taken in Hillscheid, Germany, in mid May 2002, 10 weeks after planting of rooted cuttings. The plants were growing in 14 cm plastic pots, they had not been pinched. In the following description color references are made to The Royal Horticultural Society Colour Chart. The color values were determined indoors from flowers developed in a green-house in May 2002 in Hillscheid, Germany.

Inflorescence:

*Type.*—Umbel, semi-spherically-shaped.
*Average diameter.*—110 mm.
*Average depth.*—65 mm.
*Peduncle length.*—145 mm.

*Peduncle color.*—Green, RHS 143 B.
*Pedicel length.*—23 mm.
*Pedicel color.*—Mainly reddish-brown, RHS 181 A.
*Number of flowers per umbel.*—About 25–35.

Corolla:
*Average diameter.*—51 mm.
*Form.*—Semi-double type.
*Shape.*—Flat, round outline, with the upper petals about the same size as the lower petals.
*Number of petals.*—6–7.
*Number of petaloids.*—0–1, narrow, same color as petals.
*Shape of petals.*—Obovate, base acute, upper end is rounded, margin is entire or slightly crenated at the tip.
*Size of petals.*—Upper petals: 27–29 mm long, 19–23 mm wide. Lower petals: 22–24 mm long, 19–21 mm wide.
*Color (general tonality from a distance of three meters)*.—Brilliant purple and white.
*Color of upper petals.*—Mainly RHS 74 B, and large white bases, RHS 155 D.
*Markings of upper petals.*—Fine pink veins, RHS 66 C.
*Color of lower petals.*—Mainly RHS 74 B, near margin RHS 74 A.
*Markings of lower petals.*—Absent.
*Color of lower surface of petals.*—RHS 74 C.
*Color of sepals.*—Outer surface: tips light green, RHS 143 C, lower part brown, RHS 181 A; inner surface: tips light green, RHS 144 A, main part RHS 184 B.
*Number of sepals.*—5.
*Shape of sepals.*—Linear to lanceolate, acute tip, truncate base, surface with moderate pubescence, margin entire.
*Size of sepals.*—10–12 mm long, 4 mm wide for the largest upper sepal, 2–3 mm in width for the other sepals.

Bud (just prior to petals unfolding):
*Shape.*—Elliptical.
*Color of sepals.*—Mainly light green, RHS 143 C, base: RHS 179 A.
*Color of petals.*—Between RHS 66 B and 66 C.
*Length.*—18 mm.
*Width.*—10 mm.

Reproductive organs:
*Androecium.*—7 fertile anthers, plenty pollen, yellow-orange, RHS 30 A, filaments white, RHS 155 D, to light-pink, RHS 68 B.
*Gynoecium.*—One pistil, style and stigma dark-red, RHS 53 A, stigma 5–6-lobed stigma.
*Fertility/seed set.*—Occasionally weak seed set, mainly in late summer to fall.
*Fruit.*—Oblong, about 5–6 mm wide, rostrum (beak) 38–40 mm long, Seed: Oblong, 4–5 mm long, brown, RHS 177 B.

Spring flowering response period: In Hillscheid, Germany, in 2002 plants had on average 0.7 flowers opened 8 weeks after planting of rooted cuttings.

Outdoor flower production: Continuously and moderately rich flowering, the flower count in 2002 in Hillscheid, Germany, indicated about 3.5 inflorescence per plant in mid May.

Durability: Good stability of flower color, good rain resistance.

Lastingness of the individual flower: About 7 days at 18° C., about 18 days for the umbel.

Fragrance: None.

PLANT

Foliage:
*Shape.*—Kidney-shaped, with weak lobes, cordate base with the gap between the lowest lobes open.
*Margin.*—Bi-crenate, slightly wavy.
*Texture.*—Upper surface smooth, velvety.
*Size of leaf.*—95 mm wide, 62 mm long.
*Color of upper surface.*—Deep green, approximately RHS 137 A to 137B.
*Color of zonation.*—Weak, darker green, about RHS 147 A.
*Color of lower surface.*—RHS 137 D.
*Petioles.*—50–60 mm long, 3–3.5 mm diameter, light green in color, approximately RHS 143 C.

General appearance and form:
*Stem color.*—Green, RHS 143 A to 143 B.
*Internode length.*—10–15 mm.
*Branching pattern.*—7.7 branches.
*Size of plants.*—Height 15.3 cm, width: 25.9 (10-week-old plants, as described, as measured from the top of the soil (base of the main stem) to the surface of the foliage canopy without inflorescence).

Pest/disease resistance/susceptibility: No observations to date.

I claim:

1. A new and distinct cultivar of geranium plant named 'Fip 750', as described and illustrated herein.

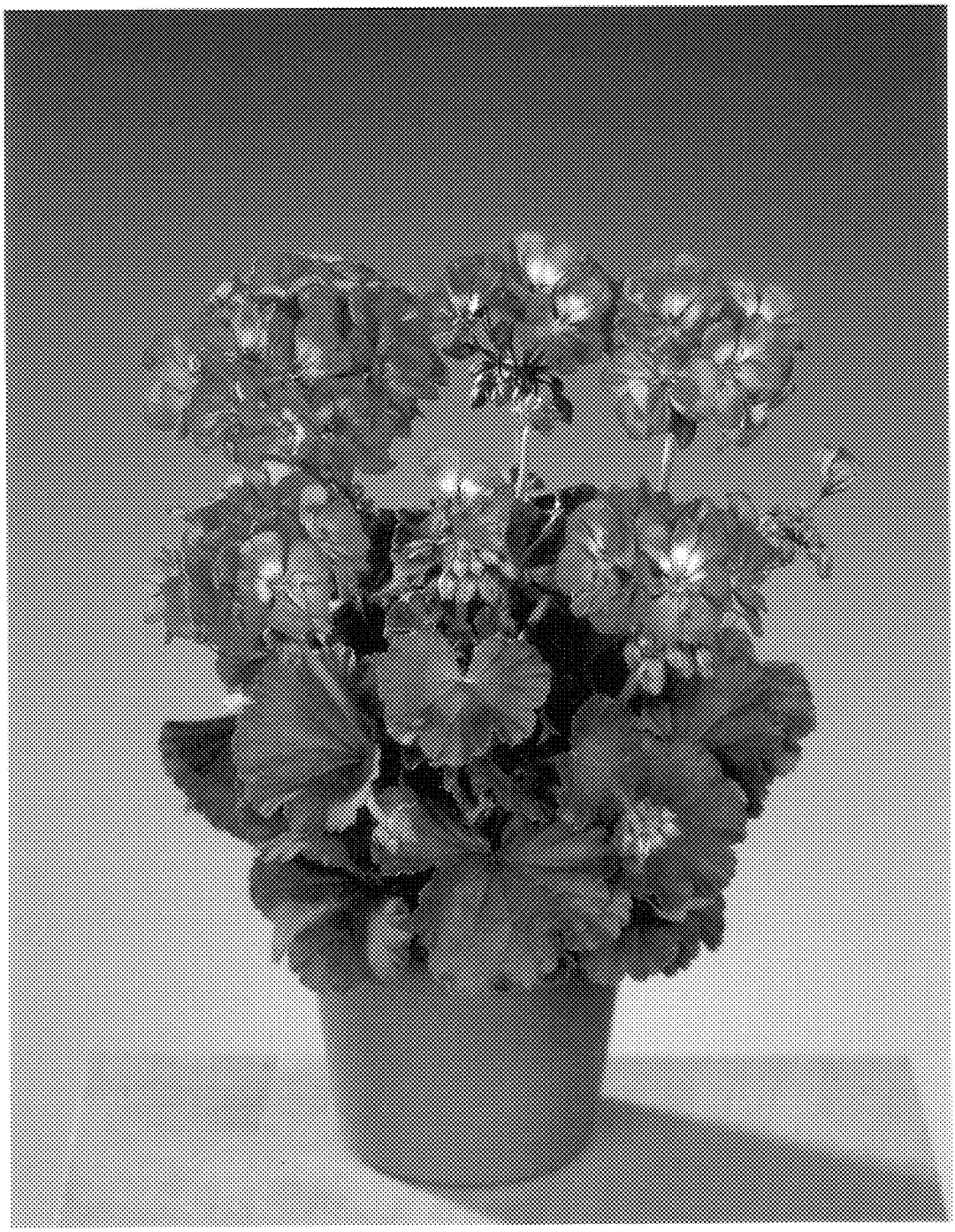

* * * * *